United States Patent
Callaghan et al.

(10) Patent No.: US 11,298,449 B2
(45) Date of Patent: Apr. 12, 2022

(54) SYSTEMS AND METHODS FOR PERFORMING MEDICAL PROCEDURES INVOLVING ACCESSING THE LYMPHATIC SYSTEM

(71) Applicants: Matthew J. Callaghan, Stanford, CA (US); Christian S. Eversull, Palo Alto, CA (US); Stephen A. Leeflang, Sunnyvale, CA (US)

(72) Inventors: Matthew J. Callaghan, Stanford, CA (US); Christian S. Eversull, Palo Alto, CA (US); Stephen A. Leeflang, Sunnyvale, CA (US)

(73) Assignee: LXS, LLC, Palo Alto, CA (US)

( * ) Notice: Subject to any disclaimer, the term of this patent is extended or adjusted under 35 U.S.C. 154(b) by 43 days.

(21) Appl. No.: 14/300,179

(22) Filed: Jun. 9, 2014

(65) Prior Publication Data

US 2014/0364765 A1    Dec. 11, 2014

Related U.S. Application Data

(63) Continuation-in-part of application No. 14/160,547, filed on Jan. 21, 2014, now Pat. No. 10,111,997, and
(Continued)

(51) Int. Cl.
| | | |
|---|---|---|
| *A61M 1/36* | (2006.01) | |
| *A61M 1/34* | (2006.01) | |
| *A61B 10/00* | (2006.01) | |

(52) U.S. Cl.
CPC ....... *A61M 1/3653* (2013.01); *A61B 10/0045* (2013.01); *A61M 1/3496* (2013.01);
(Continued)

(58) Field of Classification Search
CPC .............. A61M 1/3653; A61M 1/3609; A61M 1/3496; A61M 1/367; A61M 2202/0405;
(Continued)

(56) References Cited

U.S. PATENT DOCUMENTS 4,957,484 A * 9/1990 Murtfeldt .......... A61M 25/0074
604/102.02
5,300,022 A    4/1994 Klapper et al.
(Continued)

FOREIGN PATENT DOCUMENTS

WO    2012052920 A1    4/2012

OTHER PUBLICATIONS

Pflug, J. and J. Calnan, The Valves of the Thoracic Duct at the Angulus Venosus, Brit J. Surg, 1968, vol. 55, No. 12, December, 6 pages.
(Continued)

*Primary Examiner* — Lauren P Farrar
*Assistant Examiner* — Hamza A Darb
(74) *Attorney, Agent, or Firm* — William A. English; Vista IP Law Group LLP

(57) ABSTRACT

System and methods are provided for treating a patient that include a delivery device sized for introduction into a target site within a patient's body, a source of one or more therapeutic and/or diagnostic agents coupled to the delivery device, and a tubular member sized for introduction into the patient's vasculature to isolate the thoracic duct. Once the thoracic duct is isolated, fluid may be removed from the thoracic duct, e.g., to prevent the agents that transit from the target site into the thoracic duct from entering the patient's vasculature, and/or to modulate flow through the thoracic duct to modulate concentration and/or resident time of the
(Continued)

agents at the target site. The one or more agents may include particles sized for preferential transit into the lymphatic system.

22 Claims, 9 Drawing Sheets

Related U.S. Application Data a continuation-in-part of application No. 14/214,882, filed on Mar. 15, 2014, now Pat. No. 10,052,059.

(60) Provisional application No. 61/832,820, filed on Jun. 8, 2013.

(52) U.S. Cl.
CPC .......... *A61M 1/367* (2013.01); *A61M 1/3609* (2014.02); *A61M 1/3615* (2014.02); *A61M 1/3659* (2014.02); *A61M 2202/0405* (2013.01); *A61M 2205/3306* (2013.01); *A61M 2205/3317* (2013.01); *A61M 2230/207* (2013.01); *A61M 2230/208* (2013.01)

(58) Field of Classification Search
CPC .... A61M 2205/3306; A61M 2230/207; A61M 2230/208; A61M 2205/3317; A61M 25/10; A61M 39/0247; A61B 5/150015; A61B 5/15; A61B 10/0045; A61B 5/1405; A61B 5/145; A61B 5/14507
See application file for complete search history.

(56) References Cited

U.S. PATENT DOCUMENTS

| | | |
|---|---|---|
| 5,391,143 A * | 2/1995 | Kensey ............... A61M 27/002 604/28 |
| 5,766,151 A | 6/1998 | Valley et al. |
| 6,443,925 B1 | 9/2002 | Schaible et al. |
| 6,547,775 B1 | 4/2003 | Blyakhman |
| 2006/0100658 A1 | 5/2006 | Obana et al. |
| 2007/0032754 A1 | 2/2007 | Walsh |
| 2007/0088414 A1* | 4/2007 | Campbell ............ A61K 9/0019 607/101 |
| 2007/0282382 A1 | 12/2007 | Shuros et al. |
| 2008/0004597 A1 | 1/2008 | Lattouf et al. |
| 2008/0009719 A1 | 1/2008 | Shuros et al. |
| 2008/0097412 A1 | 4/2008 | Shuros et al. |
| 2008/0140000 A1 | 6/2008 | Shuros et al. |
| 2008/0248126 A1* | 10/2008 | Cheng .................. A61K 47/482 514/1.1 |
| 2009/0054805 A1 | 2/2009 | Boyle |
| 2010/0217346 A1 | 8/2010 | Shuros |
| 2010/0310511 A1* | 12/2010 | Zeskind ........... G01N 33/56972 424/85.5 |
| 2011/0236868 A1* | 9/2011 | Bronstein ............. G06T 19/006 434/267 |
| 2011/0276023 A1 | 11/2011 | Leeflang et al. |
| 2012/0029466 A1 | 2/2012 | Callaghan et al. |
| 2012/0134918 A1* | 5/2012 | Katti .................. A61K 51/1244 424/1.29 |
| 2012/0330132 A1 | 12/2012 | Sorajja et al. |
| 2013/0245607 A1 | 9/2013 | Eversull et al. |
| 2014/0243790 A1 | 8/2014 | Callaghan et al. |
| 2014/0303461 A1 | 10/2014 | Callaghan et al. |

OTHER PUBLICATIONS

Korean Intellectual Property Office, International Search Report and Written Opinion for corresponding International Application No. PCT/US2014/041445, Applicant: Matthew John Callaghan, dated Jun. 8, 2014, 16 pages.

European Patent Office, Search Report for corresponding European Application EP 15 808 427.0, Applicant: LXS, LLC, EPO Forms 1507S, 1703, and P04A42 ; dated Feb. 2, 2017, 10 pages.

* cited by examiner

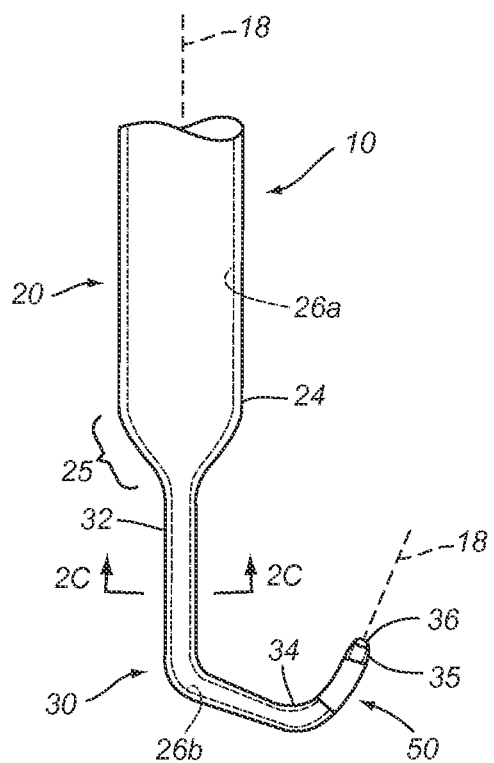
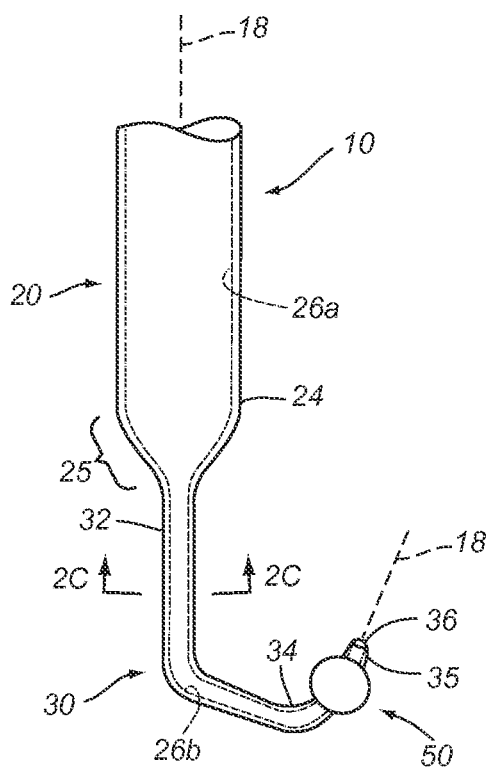
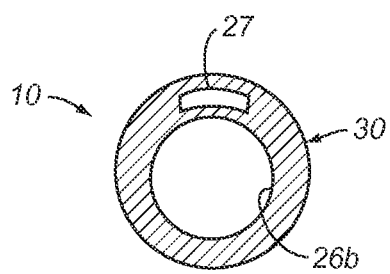

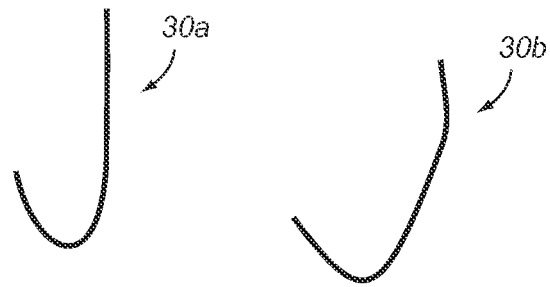
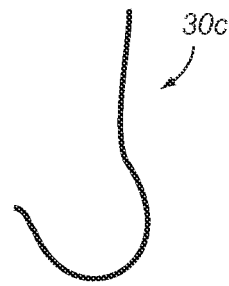
FIG. 3A
FIG. 3B
FIG. 3C
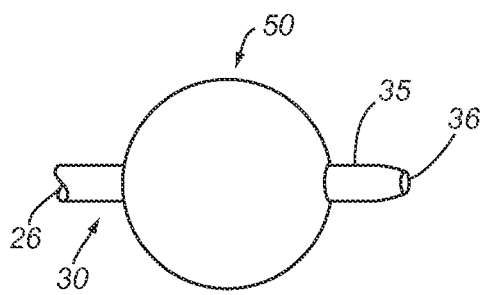
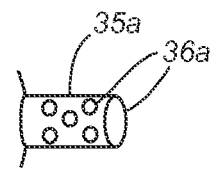
FIG. 4A
FIG. 4B
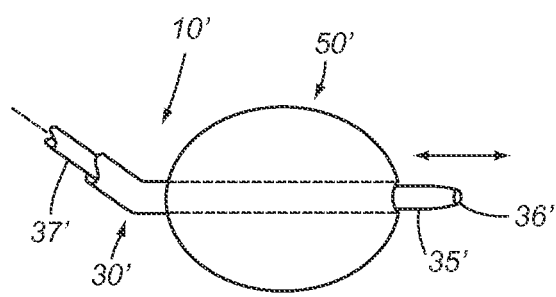
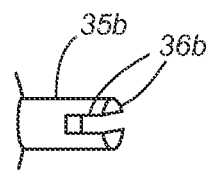
FIG. 4D
FIG. 4C

SYSTEMS AND METHODS FOR PERFORMING MEDICAL PROCEDURES INVOLVING ACCESSING THE LYMPHATIC SYSTEM

This application claims benefit of co-pending provisional application Ser. No. 61/832,820, filed Jun. 8, 2013, and is a continuation-in-part of co-pending application Ser. No. 14/160,547, filed Jan. 21, 2014, and Ser. No. 14/214,882, filed Mar. 15, 2014, the entire disclosures of which are expressly incorporated by reference herein.

FIELD OF THE INVENTION

The present invention relates generally to apparatus and methods used to perform medical procedures, and, more particularly, to systems and methods for performing medical procedures that include accessing and/or otherwise involving the lymphatic system of a patient, e.g., to facilitate localized delivery and/or removal of compounds, e.g., therapeutic and/or diagnostic compounds introduced into a patient's body.

BACKGROUND

Cancer is the second leading cause of death in the United States. Current treatments focus on surgical excision of cancerous tissue, radiation, systemic and localized chemotherapy and more recently immunotherapy. Using systemic chemotherapy, it is difficult to deliver high doses specifically to tumor cells without affecting surrounding tissue and triggering severe systemic side effects. Furthermore, although a high percentage of tumor cells metastasize through the lymphatic system, raising drug levels in the lymphatic system has proven especially challenging.

The lymphatic system includes a network of vessels generally separate from veins and arteries. Rather than whole blood, the lymphatic vessels carry lymphatic fluid (or lymph). The lymphatic system serves a variety of physiologic purposes, including returning interstitial fluid to the vascular space, transporting fats from the digestive tract, and transporting immune-mediating cells. The composition of lymphatic fluid is similar to plasma. It contains white blood cells, but generally does not contain red blood cells, platelets, or various other components of whole blood. The lymphatic system culminates in a single large channel called the thoracic duct, which joins the central venous system at the confluence of the left internal jugular and subclavian veins.

Historically, the lymphatic system has been directly accessed rarely in medical procedures. For example, some diagnostic procedures involve direct cannulation of peripheral lymphatic vessels, e.g., to infuse dye for identification of lymph nodes. Direct access of the central lymphatic vessels, such as the thoracic duct, is generally avoided. For example, a defect created in the thoracic duct generally does not readily close on its own, leading to significantly morbid conditions, such as chylothorax (persistent collection of lymphatic fluid around the lungs).

The lymphatic system does, however, eventually drain into the vasculature. A majority of lymphatic vessels come to a confluence in the thoracic duct which generally enters the venous system at the junction of the left subclavian vein and the left internal jugular vein. A series of valves generally facilitate one-way flow of lymphatic fluid into the venous system and prevent reflux of whole blood into the thoracic duct. Although not well studied, disruption of one or more of these valves may have negative consequences. Therefore, it may be desirable to protect these valves and/or the lymphatic vessels themselves from damage.

SUMMARY

The present invention is directed generally to systems and methods for performing medical procedures. More particularly, the present invention is direct to systems and methods for performing medical procedures that include accessing the lymphatic system of a patient, e.g., to remove, separate, and/or re-infuse lymphatic fluid, e.g., to facilitate localized delivery of therapeutic and/or diagnostic agents and/or removal of such agents within the lymphatic system.

The lymphatic system is a network of channels draining local and regional lymph nodes and carrying protein, lymphocytes, and plasma from the interstitium back to the venous circulation. The lymphatic system culminates in a single large channel called the thoracic duct, which joins the central venous system at the confluence of the left internal jugular and subclavian veins. At the level of the capillary bed, lymphatic channels consist of overlapping fenestrations, permitting uptake of macromolecules and compounds too large to return through venous capillaries.

It has been shown that interstitially injected compounds or particles smaller than about one hundred nanometers (100 nm) but larger than about thirty to forty nanometers (30-40 nm) pass freely from the interstitium into the lymphatic capillary channels. Compounds larger than about one hundred nanometers (100 nm) remain confined to the site of injection, while compounds smaller than about forty nanometers (40 nm) may pass into venous capillaries. Uptake and passage may be further affected by charge and shape of the compounds.

Recently, new formulations of existing chemotherapy agents have been designed to reduce systemic complications by prolonged circulation time and preferential residence in interstitial tissues. Liposomal formulations have proven the most efficient and are available for intravenous injection in end-stage cancers of the breast, ovary, and lung.

In a similar manner, carriers for chemotherapeutic agents may be specifically designed for preferential uptake by local lymphatic channels when injected either directly into or adjacent to cancerous tissue. Recent animal studies using liposomal preparations of doxorubicin demonstrate this principle. However, while this technique may improve drug concentration in lymphatic channels, it does not limit systemic toxicity. The injected drug will eventually collect in the thoracic duct and be returned to the venous circulation, e.g., within approximately twenty four (24) hours. The systems and methods described herein may facilitate local drug concentration in and around a tumor while limiting systemic side effects by using the lymphatic system.

Another limitation of current methods is a dependence on peripheral blood samples to monitor for circulating tumor cells. Recent technology has advanced detection of these cells in peripheral blood although cells in circulation are still quite rare. Tumor cells are known to transit the lymphatic system, sometimes preferentially, and therefore detection methods to analyze cells within lymphatic fluid would be of significant benefit in cancer detection and treatment.

The systems and methods herein may facilitate accessing and capturing lymphatic output from the thoracic duct. Flow may be monitored, regulated (including flow rate), diverted, discarded, and/or selectively returned to circulation. Thus, in the setting of cancer therapy, therapeutic agents may be introduced into the body in such a way that at least part of the agents ultimately transits the lymphatic system. In an exemplary embodiment, such agents may be designed to preferentially move into and transit within the lymphatic system. Such agents may be introduced locally into tissue, intravenously, intra-arterially, or into other body cavities. Alternatively, agents may be introduced directly into the lymphatic system in either antegrade or retrograde directions.

Subsequently, output from the thoracic duct (or other lymphatic channel) may be monitored, regulated, diverted, discarded, and/or selectively returned to the body (e.g., intravenously or otherwise). This may be done in such a way as to control dwell time and/or transit, capture, removal, and/or recirculation of toxic chemotherapeutic agents. In this manner, the effects of the agents may be concentrated in local tissue (e.g., at a tumor site) or within the lymphatic system (e.g., at the site of metastatic or primary cancer cells) while minimizing exposure to the remainder of the body, thus limiting toxicity.

In an exemplary embodiment, one or more agents may be introduced locally in or around the site of a breast tumor. The agent(s) may be sized or otherwise designed to cause preferential uptake by the lymphatic system. The rate of local depletion may be modulated by controlling the flow rate through the thoracic duct, for example, by selective occlusion or flow restriction, e.g., using a catheter or other device positioned within the thoracic duct. Further, in addition or alternatively, the output of the thoracic duct may be captured and discarded, such that lymph that contains the agent(s) at relatively high levels is not re-circulated within the body, which would otherwise cause systemic exposure. In this manner, local concentrations and time of exposure of toxic chemotherapeutic agents may be increased at the site of therapy without incurring substantially deleterious systemic side effects.

In accordance with an exemplary embodiment, a system is provided for treating a patient that includes a delivery device sized for introduction into a target treatment site within a patient's body; a source of one or more agents coupled to the delivery device, the one or more agents comprising particles sized for preferential transit into the lymphatic system; and a tubular member comprising a proximal end, a distal end sized for introduction into the patient's body into a thoracic duct, an expandable member on the distal end for substantially sealing the thoracic duct from the patient's venous system, and a lumen extending between the proximal and distal ends for removing fluid from the thoracic duct including the particles transiting into the thoracic duct.

In accordance with another embodiment, a method is provided for treating a patient that includes delivering one or more agents into a target treatment site within a patient's body, the one or more agents comprising particles sized for preferential transit into the lymphatic system; introducing a distal end of a tubular member into the patient's vasculature via a percutaneous access site; advancing the tubular member until the distal end is disposed within a junction of the patient's left internal jugular vein and left subclavian vein and adjacent the patient's thoracic duct; sealing the thoracic duct using the distal end of the tubular member to substantially isolate the thoracic duct from the junction; and removing fluid from the thoracic duct through the tubular member to a location exterior to the patient's body, thereby removing particles from the one or more agents that have transited into the thoracic duct.

In accordance with still another embodiment, a method is provided for minimizing systemic exposure to one or more therapeutic or diagnostic agents that includes locally introducing the one or more agents into a patient's body, and subsequently collecting and/or removing lymphatic fluid from the patient's thoracic duct. For example, the one or more agents may be sized for preferential uptake by the patient's lymphatic system, and the thoracic duct may be isolated to prevent the one or more agents that transit into the thoracic duct from entering the patient's venous system. Instead, the one or more agents may be removed from the thoracic duct when the lymphatic fluid is removed.

In accordance with yet another embodiment, a method is provided for modulating one or both of residence time and concentration of one or more therapeutic or diagnostic agents that includes delivering the one or more agents locally into a target site within a patient's body, and modulating flow of fluid through the patient's thoracic duct.

Other aspects and features of the need for and use of the present invention will become apparent from consideration of the following description taken in conjunction with the accompanying drawings.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments. The drawings illustrate exemplary embodiments of the invention, in which:

FIGS. 2A and 2B are details of a distal portion of the apparatus of FIG. 1, showing a balloon on the distal portion in collapsed and enlarged configurations, respectively.

FIG. 2C is a cross-section of the distal portion of the apparatus of FIGS. 2A-2B taken along line 2C-2C.

FIGS. 3A-3C are schematic views showing alternative relaxed shapes for the distal portion of an apparatus, such as that shown in FIG. 1.

FIGS. 4A-4C are details of alternative embodiments of distal tips that may be provided on an apparatus, such as that shown in FIGS. 1-2B.

FIG. 4D is a detail of another alternative embodiment of a retractable/advanceable distal tip that may be provided on an apparatus, such as that shown in FIGS. 1-2B.

DETAILED DESCRIPTION OF THE EXEMPLARY EMBODIMENTS

Figure 1:
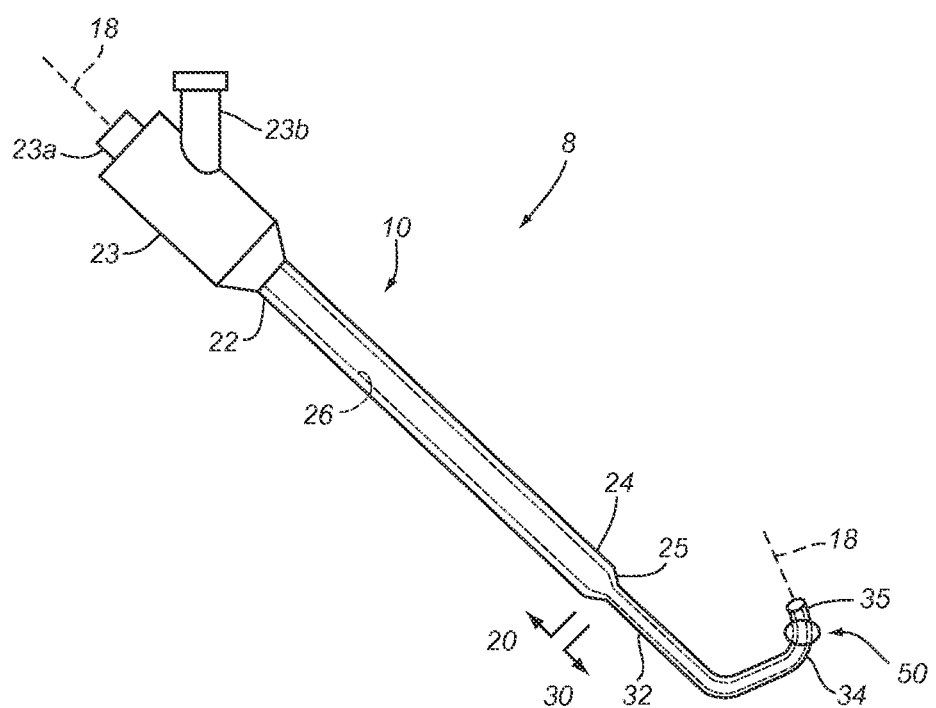
FIG. 1 is a perspective view of an exemplary embodiment of an apparatus for accessing a thoracic duct.

Turning to the drawings, FIGS. 1-2B show an exemplary embodiment of an apparatus 8 for accessing and/or isolating the lymphatic system of a patient 90 (not shown, see, e.g., FIG. 5 for anatomical references), e.g., to aspirate or otherwise draw lymphatic fluid from the thoracic duct 94, as described further below. Generally, the apparatus 8 includes a catheter or other tubular member 10 including a proximal or main portion 20, e.g., sized and/or shaped for introduction into a blood vessel of the patient, such as a jugular vein 92b (not shown, see FIG. 5), and a relatively smaller distal portion 30, e.g., sized and/or shaped for introduction into a thoracic duct 94 of the patient 90 (also not shown, see FIG. 5), thereby defining a central longitudinal axis 18 for the apparatus 8.

A balloon or other expandable member 50 may be provided on the distal portion 30, e.g., sized for introduction into a thoracic duct in a collapsed configuration and expandable to an enlarged configuration for substantially sealing and/or isolating the thoracic duct 94, as described further below. The balloon 50 may be formed from elastic material, e.g., such that the balloon 50 may be inflated to multiple diameters to accommodate engaging the wall of thoracic ducts of various sizes and/or shapes, to provide a substantially fluid-tight seal without applying excessive forces against the wall.

Figure 5:
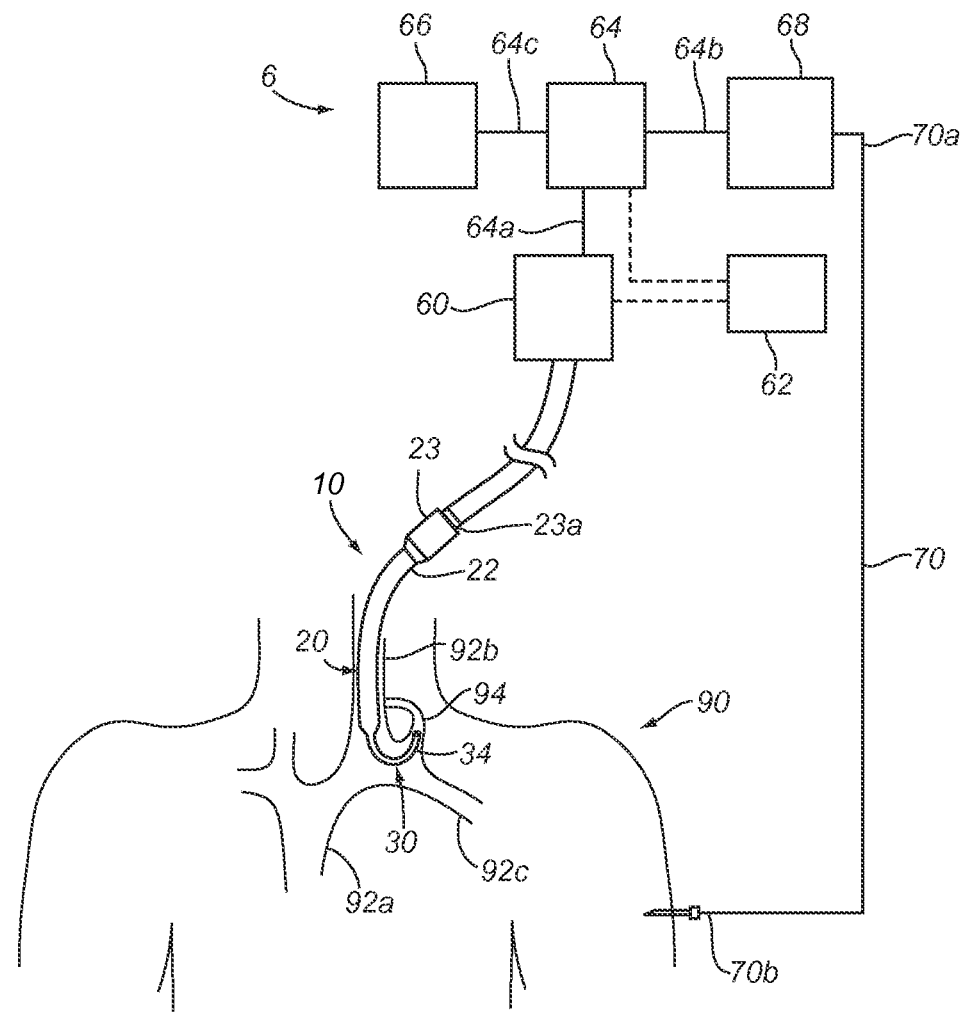
FIG. 5 is a detail of a patient's body showing a schematic of an exemplary system for accessing the lymphatic system of the patient including an apparatus, such as that shown in FIGS. 1-2B.

Generally, the proximal and distal portions 20, 30 of the catheter 10 have different dimensions and/or properties. For example, the proximal portion 20 may have a substantially straight shape in a relaxed state, yet may be sufficiently flexible to be introduced into a patient's body 90, e.g., sufficiently flexible to be introduced into the venous system from a percutaneous access site, such as via a left or right internal or external jugular vein, subclavian vein, axillary vein, or other percutaneous access site. In an exemplary embodiment, access may be gained from the left internal jugular vein 92b to approach the junction of the left internal jugular vein 92b and left subclavian vein 92c, as shown in FIG. 5. The distal portion 30 may have a curvilinear shape in a relaxed state, e.g., a simple curved shape or a more complicated shape including one or more curved and/or straight sections, which may facilitate introduction of the distal portion 30 into the thoracic duct 94, e.g., from the jugular vein 92b, as described further below.

In addition or alternatively, the proximal portion 20 may be substantially longer than the distal portion 30, e.g., to allow the proximal portion 20 to be introduced into the patient's body from an access site, e.g., into the left internal jugular vein 92b, and manipulated to introduce the distal portion 30 into the thoracic duct 94. For example, as shown in FIG. 1, the proximal portion 20 may include a proximal end 22 including a handle or hub 23, and a distal end 24 coupled or otherwise including a transition 25 to the distal portion 30. In exemplary embodiments, the proximal portion 20 may have a length from the handle 23 to the transition 25 between about three and one hundred twenty centimeters (3.0-120 cm), or alternatively between about three and thirty centimeters (3.0-30.0 cm), and may have an outer diameter or other maximum cross-section between about one and seven millimeters (1.0-7.0 mm), or alternatively between about one and three millimeters (1.0-3.0 mm). The handle 23 may be larger than the proximal portion 20, e.g., having a shape and/or otherwise configured for holding and/or manipulating the catheter 10 from a location outside of a patient's body.

The transition 25 may include a tapered shape, as shown, an abrupt step-down shape (not shown), and the like to transition between the proximal and distal portions 20, 30. If the proximal and distal portions 20, 30 are formed from different materials, the transition 25 may connect the different materials together, e.g., by bonding with adhesive, fusing, sonic welding, heat forming, and the like.

The distal portion 30 may have a proximal end 32 extending distally from the transition 25, e.g., aligned substantially axially with the proximal portion 20, and a distal end 34 terminating in a distal tip 35. In exemplary embodiments, the distal portion 30 may have a length from the proximal end 32 to the distal tip 35 between about one and ten centimeters (1.0-10.0 cm), and may have an outer diameter or other maximum cross-section between about half to five millimeters (0.5-5.0 mm), or alternatively between about half and two millimeters (0.5-2.0 mm). Thus, the distal portion 30 may be substantially shorter than the proximal portion 20, e.g., such that the proximal portion 20 may extend from a percutaneous access site (not shown) into the junction of the left internal jugular vein 92b and the left subclavian vein 92c, and the distal portion 30 may simply curve and enter the thoracic duct 94, as described further elsewhere herein.

The distal portion 30 may have a substantially uniform outer diameter between the proximal end 32 and the distal tip 35, or the diameter may vary, e.g., tapering at or adjacent the distal tip 35 to provide a substantially atraumatic distal tip 35.

In addition, the distal portion 30 may have a flexibility greater than the proximal portion 20. For example, the proximal portion 20 may have sufficient column strength, stiffness, torque, and the like such that the proximal portion 20 may be manipulated from the handle 23 without substantial risk of the distal end 24 of the proximal portion 20 buckling or kinking, while providing sufficient flexibility to accommodate introduction into curved vessels within the patient's body. In exemplary embodiments, the proximal portion 20 may have a substantially rigid or semi-rigid proximal end 22, e.g., to facilitate advancement of the distal portion from the handle 23, while the distal end 24 may be semi-rigid or flexible. Moreover, the device properties may be optimized to responsively translate manipulation of the proximal end 22 into movement of the distal portion 30, e.g. by means of rotation, torque, angular manipulation, withdrawal, and/or advancement.

The distal portion 30 may be substantially flexible, e.g., biased to the curvilinear shape when free from external forces, yet flexible to accommodate bending, compressing (of the distal tip 35 towards the proximal portion 20), and/or other movement of the distal portion 30 to facilitate introducing the distal tip 35 into the thoracic duct. In exemplary embodiments, the distal portion 30 may be formed from PEBAX, urethane, silicone, and/or other soft and/or flexible materials, e.g., having substantially uniform properties along the length of the distal portion 30, or becoming progressively (or otherwise) softer and/or more flexible from the proximal end 32 to the distal tip 35. The proximal and distal portions 20, 30 may be formed from different materials to provide the desired flexibility. For example, the proximal portion 20 may include a reinforcement layer, e.g., braiding and the like between inner and outer layers (not shown), while the distal portion 30 may simply include a single layer or vice versa. Alternatively, a different reinforcing layer (e.g. braid, coil, stent-like structure or other scaffolding) may be used in the proximal and distal portions 20, 30. For example, a reinforcing structure may include a laser-cut tubular structure (e.g., formed from Nitinol, stainless steel, cobalt chromium, and the like) having a structure that may accommodate a substantially straight shape and a desired curvilinear shape without substantial permanent deformation. Further, a reinforcing structure may be shape set (e.g., by heat treating, annealing, plastically deforming, and the like) in order to maintain a desired curvilinear shape in the distal portion 30.

In addition or alternatively, relative flexibility may be obtained by providing different wall thicknesses, e.g., from the same or different materials. For example, as shown in FIGS. 2A and 2B, the proximal portion 20 may have a relatively larger wall thickness than the distal portion 30, which may enhance relative flexibility of the distal portion 30. In exemplary embodiments, the wall thickness of the proximal portion 20 may be between about 0.1 and three millimeters (0.1-3.0 mm), while the wall thickness of the distal portion 30 may be between about 0.1 and two millimeters (0.1-2.0 mm).

As shown in FIG. 1, the distal portion 30 may include multiple substantially straight sections between curved sections, e.g., to provide a "hook" shape having an overall angle of curvature equal to or greater than ninety degrees, e.g., between about ninety and three hundred sixty degrees)(90-360°, or between about ninety and one hundred fifty degrees)(90-150°. Such radii of curvature may facilitate introduction into the thoracic duct 94, which may connect near the junction of the jugular, subclavian, and brachiocephalic veins 92 at an acute angle, such that a radius of curvature greater than ninety degrees)(90° may be necessary to align the distal tip 35 with the thoracic duct 94 when the proximal portion 20 is within the left internal jugular vein 92b, as described further elsewhere herein.

In an alternative embodiment, shown in FIG. 3A, the distal portion 30a may include a single substantially continuous radius of curvature approaching one hundred eighty degrees)(180°. In a further alternative, shown in FIG. 3B, the distal portion 30b may have a more complicated curvilinear shape, e.g., including a first straight section between a bend and a radiused section ending in a substantially straight distal tip (which may carry a balloon, not shown). In yet another alternative, shown in FIG. 3C, the distal portion 30c may include a continuous curved shape including a first bend in an opposite direction to the main radius of curvature of the distal portion 30c. Such shapes may orient the distal tip 35 of the catheter 10 back towards the proximal end 22 with the distal tip 35 defining a desired angle relative to the longitudinal axis 18 within the proximal portion 20.

In still another alternative, the distal portion 30 may include a curved section of constant or variable radius having an arc angle of between about zero and three hundred sixty degrees)(0°-360° and a radius of curvature between about one and fifteen millimeters (1.0-15.0 mm). Further alternatively, the distal portion 30 may include one or more discrete bends, creating a distal shape having a width between about two and thirty millimeters (2.0-30.0 mm). More generally, any of the foregoing shapes may be optimized to locate the distal tip 35 at or near the thoracic duct ostium and simultaneously align the tip vector with the entry vector of the thoracic duct 94. Furthermore, the shape of the distal portion 30 may be sufficiently resilient to return to its pre-set shape, e.g. after introduction through a sheath, repeated manipulation, and the like.

Optionally, the distal portion 30 may include one or more features to facilitate identification and/or localization of the distal portion 30, e.g., the balloon 50 and/or distal tip 35, within a patient's body using external imaging. For example, one or more echogenic features, may be provided on or in the wall of the balloon 50 and/or on the distal tip 35, which may facilitate monitoring the distal portion 30 using ultrasound imaging. Such exemplary features may include doping or coating with tungsten, tungsten carbide, titanium dioxide, iron oxide, zinc oxide, platinum, gold, barium, bismuth, and/or titanium; echogenic surface modifications such as reflective gratings, surface depression and/or projections; inclusions, for example, of glass particles, air bubbles, and the like, including those described in U.S. Pat. No. 5,921,933, the entire disclosure of which is expressly incorporated by reference herein. Alternatively, radiopaque and/or other markers (also not shown) may be provided to facilitate monitoring the distal portion 30 using fluoroscopy or other external imaging.

Returning to FIGS. 1-2B, the catheter 10 may include one or more lumens 26, 27 extending therethrough, e.g., from the proximal end 22 of the proximal portion 20 to the distal portion 30. For example, as shown in FIG. 1, an aspiration or infusion lumen 26 may be provided that communicates with a port 23a in the handle 23 and extends through the entire proximal and distal portions 20, 30 to one or more inlet (or outlet) ports 36 adjacent the distal tip 35. As best seen in FIGS. 2A and 2B, the aspiration lumen 26 may include a relatively large region 26a within the proximal portion 20 and a relatively small region 26b within the distal portion 30. In exemplary embodiments, the proximal region 26a of the lumen 26 may have an inner diameter (or other maximum cross-section) between about one and five millimeters (1.0-5.0 mm), while the distal region 26b may have an inner diameter (or other maximum cross-section) between about 0.1 and three millimeters (0.1-3.0 mm).

The smaller diameter of the distal region 26b may allow the outer diameter of the distal portion 30 to be minimized, e.g., to provide desired flexibility and/or minimize the size of the distal portion 30 to facilitate introduction into the thoracic duct 94, while the larger diameter of the proximal region 26a may allow lymph or other fluids to be drawn through the catheter 10 more easily. For example, the larger diameter over most of the length of the catheter 10 may expose the fluid to lower friction, which may increase flow rate and/or reduce the risk of lysing or otherwise damaging cells or other components of the fluid being aspirated or delivered through the lumen 26 of the catheter 10.

As shown in FIGS. 2A, 2B, and 4A, the aspiration lumen 26 may communicate with a single inlet port 36 in the distal tip 35, e.g., aligned with the central longitudinal axis 18. Alternatively, multiple inlet ports may be provided on the distal tip, e.g., to reduce the risk of a single or multiple ports becoming occluded with fluid or debris and/or contacting and sucking the wall of the thoracic duct or other body lumen against the distal tip 35, which may otherwise prevent fluid from being drawn into the lumen 26. For example, as shown in FIG. 4B, the distal tip 35a may include a plurality of side ports in addition to the axial inlet port 36a, or, as shown in FIG. 4C, one or more slots (two shown) may be provided that extend partially from the axial inlet port 36b.

In addition, turning to FIG. 2C, the catheter 10 may include an inflation lumen 27, e.g., extending through the proximal and distal portions 20, 30 and communicating with an interior of the balloon 50. The inflation lumen 27 may communicate with a port 23b on the handle 23, shown in FIG. 1, which may allow a source of inflation and/or vacuum, e.g., a syringe and the like (not shown), to be coupled to the catheter 10 and communicate with the interior of the balloon 50, e.g. to allow the balloon 50 to be inflated and collapsed, as described elsewhere herein. Alternatively, another expanded member, e.g., a mechanically expandable frame and the like (not shown, see, e.g., FIGS. 9A-9C), may be provided on the distal portion 30 instead of the balloon 30. In this alternative, a mechanical actuator, e.g., a slider, wheel, and the like (also not shown, may be provided on the handle 23 that is coupled to the frame or other expandable member for directing the expandable member between collapsed and enlarged configurations.

Optionally, the catheter 10 may include one or more additional lumens, if desired. For example, an infusion lumen (not shown) separate from the aspiration lumen 26 may be provided, which may allow infusion of fluids or agents through the catheter 10 to one or more outlets (also not shown) on the distal portion 30, independent of aspiration or removal of fluid through the lumen 26. Infusion of fluids may be into the thoracic duct 94 or into the vein(s) at any point along the course of the catheter 10. Infused fluids may include at least some part or all of fluids aspirated by means of the same catheter. In addition, a guidewire lumen and/or a stylet lumen (not shown) may be provided that extends through the proximal portion 20 into the distal portion 30, e.g., for at least partially straightening and/or supporting the distal portion 30 during introduction into a patient's body, as described elsewhere herein.

Figure 6:
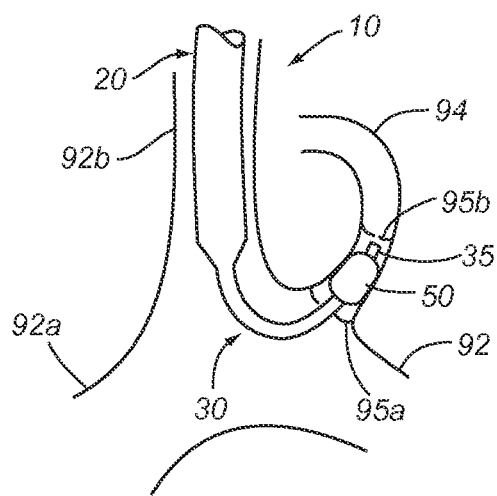
FIG. 6 is a detail of a patient's body, showing the distal portion of a catheter positioned within a thoracic duct of the patient and with a balloon thereon inflated to substantially isolate the thoracic duct from the patients venous system.

Turning to FIGS. 5 and 6, the apparatus 8 may be used to perform a medical procedure within the patient's body 90 that includes accessing the thoracic duct 94, which may be related to any of the conditions and/or treatments described elsewhere herein. Initially, the catheter 10 may be introduced into the patient's body 90, e.g., into the venous system from a percutaneous access site, such as the left or right internal or external jugular, subclavian, axillary, anterior cubital, or femoral veins.

To facilitate introduction and/or navigation of the catheter 10, one or more other devices may be used in conjunction with the catheter 10, if desired. For example, in one embodiment, a guidewire (not shown) may be introduced and advanced from the percutaneous access site, through any intervening vessels into the junction of the left internal jugular vein 92b and left subclavian vein 92c, and into the thoracic duct 94. The guidewire may be backloaded into the inlet port 36 of the distal portion 30 and through the aspiration lumen 26 (or through a separate lumen, e.g., a dedicated guidewire lumen, not shown, if provided on the catheter 10). The catheter 10 may then be advanced over the guidewire into the access site and intervening vessels, and at least the distal tip 35 of the distal portion 30 may be introduced into the thoracic duct 94.

In addition or alternatively, other devices may be used to at least partially straighten and/or otherwise support the distal portion 30 of the catheter 10. For example, a stylet (not shown) may be positioned within the catheter 10, e.g., within the aspiration lumen 26 or a separate lumen (not shown) such that the stylet enters at least partially into the distal portion 30, thereby directing the distal portion 30 from its relaxed curvilinear shape to a less curved or substantially straight configuration (not shown) and/or otherwise supporting the distal portion 30 from buckling or kinking. The distal portion 30 may then be introduced through the access site and any intervening vessels until the distal tip 35 is located adjacent the thoracic duct 94, e.g., within the junction of the jugular and subclavian veins 92b, 92c. The stylet may be sufficiently flexible to accommodate introducing the distal portion 30 through any bends or tortuous anatomy encountered between the access site and the thoracic duct 94. Once the distal tip 35 is located adjacent the thoracic duct 94, e.g., within the junction of the left internal jugular vein 92b and the left subclavian vein 92b, the stylet may be removed, thereby allowing the distal portion 30 to return towards its relaxed, curvilinear configuration. Alternatively, one or more shaped stylets may be used to accentuate, alter, essentially create the shape of the distal portion 30. Further, a stylet may be used to direct the distal portion 30 toward and/or into the thoracic duct 94, e.g., by independent and/or co-manipulation (e.g. twisting, advancing, retracting) of the stylet and the catheter 10.

In another alternative, a sleeve, sheath, cover, and the like (also not shown) may be provided over the catheter 10 until the distal portion 30 is sufficiently covered, e.g., to at least partially straighten and/or support the distal portion 30. The distal portion 30 may then introduced into the patient's body 90 until the distal tip 35 is disposed adjacent the thoracic duct 94, whereupon the cover may be removed to expose and release the distal portion 30, again thereby allowing the distal portion 30 to return towards its relaxed, curvilinear configuration.

With the distal portion released or exposed within the junction, the proximal portion 20 of the catheter 10 may then be manipulated, e.g., advanced and/or retracted, rotated, and the like until the distal tip 35 enters the thoracic duct 94, as shown in FIG. 5. For example, without a guidewire, the catheter 10 may be manipulated until the distal portion 30 "hooks" the ostium of the thoracic duct 94. Because of the soft and/or flexible nature of the distal portion 30, such manipulation may be completed without substantial risk of perforation or other damage to the vessels. In addition, given that the thoracic duct 94 may extend at an angle almost one hundred eighty degrees relative to the left internal jugular vein 92b, the angle of the distal portion 30 may facilitate orienting the distal tip 35 "backwards" towards the ostium of the thoracic duct 94.

Once the distal tip 35 is placed within the ostium of the thoracic duct 94, the catheter 10 may be retracted or otherwise manipulated to direct the distal portion 30 further into the thoracic duct 94. For example, if the catheter 10 is to be introduced into the left internal jugular vein 92b, as shown in FIG. 5, the length of the catheter 10 may be substantially shorter than most catheters, thereby providing a more direct relationship of movement between the proximal end 22 and the distal portion 30 since the catheter 10 is less likely to twist, compress, stretch, and the like between the proximal end 22 and the distal portion 30.

If the catheter 10 is manipulated to place the distal tip 35 at the ostium of the thoracic duct 94, the catheter 10 may simply be retracted (e.g., upwardly) to pull the distal tip 35 up into the thoracic duct 94, e.g., as shown in FIG. 6. In an exemplary embodiment, the distal portion 30 may pass through the terminal valve 95a of the thoracic duct 94 until the balloon 50 is positioned between the terminal valve 95a and the next valve 95b within the thoracic duct 94. The balloon 50 may then be inflated to engage the wall of the thoracic duct 94 and substantially seal and/or isolate the thoracic duct 94 from the veins 92.

Optionally, navigation to the thoracic duct 94 may be aided using external imaging, such as ultrasound imaging. For example, as described elsewhere herein, the distal portion 30 of the catheter 10 may include one or more echogenic features, which may facilitate identification and monitoring the balloon 50 and/or the distal tip 35. Because the thoracic duct 94 is located near the surface, i.e., close to the patient's skin, an ultrasound imaging device placed on or near the patient's skin may provide high resolution visualization of the region including the thoracic duct 94 and adjacent veins 92 to facilitate monitoring the distal portion 30 until the distal tip 35 and balloon 50 are positioned as desired.

In addition or alternatively, tactile feedback and/or manipulation may be used to facilitate positioning the distal portion 30. For example, given the close proximity of the thoracic duct 94 and neighboring veins 92 to the skin, it may be possible to feel the catheter 10 by placing the user's fingers on the patient's overlying skin and pressing against the skin and intervening tissues. Such pressure may also be used to physically manipulate the distal portion 30, e.g., in addition to manipulation of the proximal end 22, to direct the distal tip 35 into the thoracic duct 94.

In addition or alternatively, other imaging may be used, such as fluoroscopy, MRI, CT, and/or direct visualization, e.g., using an imaging element carried on the distal portion 30 of the catheter 10. Exemplary imaging elements and methods for using them are disclosed in U.S. Publication Nos. 2011/0034790, 2007/0015964, 2006/0084839, and 2004/0097788, the entire disclosures of which are expressly incorporated by reference herein.

Optionally, additional methods may be used to facilitate introducing the distal tip 35 and balloon 50 through the terminal valve 95*a*, e.g., instead of simply pushing the distal tip 35 through the valve 95*a*. For example, the terminal valve 95*a* may be monitored using external imaging or otherwise monitored to coordinate timing of movement of the terminal valve 95*a* with physiological events, e.g., heart rate, and the like, until the terminal valve 95*a* naturally opens, whereupon the distal tip 35 may be advanced through the open valve 95*a* into the thoracic duct 94. Alternatively, the user may trigger opening of the terminal valve 95*a*, e.g., by increasing lymph within the patient's body, for example, by squeezing tissue in the arm or leg.

In another alternative, a negative pressure may be created within the junction, e.g., by aspirating into the catheter 10 or otherwise, with the resulting vacuum causing the terminal valve 95*a* to open and allow the distal tip 35 to be advanced into the thoracic duct 94. In other alternatives, the user may simply periodically probe the terminal valve 95*a* by gently advancing the distal tip 35 against the valve 95*a* and/or by rotating the catheter 10 to screw the distal tip 35 through the valve 95*a*. Further alternatively, the balloon 50 (or other distal expandable member) may be at least partially expanded to assist in centering the distal tip 35 in or near the ostium in order to more easily cross the valve 95*a*.

In yet another alternative, a helical tip member (not shown) may be provided on the distal portion 30 that extends from the distal tip 35, which may be rotated to guide the distal tip 35 through the terminal valve 95*a*. In these alternatives, the distal portion 30 may pass through the terminal valve 95*a* until the balloon 50 is positioned between the terminal valve 95*a* and the next valve 95*b* within the thoracic duct 94. The balloon 50 may then be inflated to engage the wall of the thoracic duct 94 and substantially seal and/or isolate the thoracic duct 94 from the veins 92.

With the balloon 50 expanded to substantially isolate the thoracic duct 94, fluid may be aspirated into the lumen 26 of the catheter 10 and collected, e.g., as described elsewhere herein, fluid may be delivered into the thoracic duct 94, and/or other desired procedures may be performed via the thoracic duct 94.

In an alternative embodiment, shown in FIG. 4D, the catheter 10' may include a movable distal tip 35,' which may be directed axially closer to or away from the balloon 50.' For example, the balloon 50' may be attached to the distal end of an outer tubular member 30,' and an inner tubular member 37' may extend through the outer tubular member 30' and the balloon 50,' and terminate in the distal tip 35.' Thus, movement of the inner tubular member 37' relative to the outer tubular member 30' may move the distal tip 35' relative to the balloon 50.' In this alternative, the balloon 50' may serve to substantially center the distal tip 35' relative to the valve(s) 95 within the thoracic duct 94 (not shown in FIG. 4D), e.g., such that the distal tip 35' may be advanced or retracted as desired relative to the valve(s) 95 to facilitate access, removal of fluid, and/or performing other procedures within the thoracic duct 94.

Optionally, the suction pressure used to aspirate lymph within the thoracic duct 94 may be adjusted, e.g., to substantially match the individual patient's maximum lymph flow. If the patient lymph flow changes over time, this method anticipates adjustment of pressure over time, both decreasing suction pressure over time, and increasing suction pressure over time, as desired.

In another option, fluids or other substances may be infused into the thoracic duct 94 or vein via the catheter 10, if desired, e.g., in a substantially continuous or oscillatory manner. For example, one or more of the following may be infused: blood contaminated lymph, lymph with greater concentrations of desired substances, and the like, as described elsewhere herein.

In another embodiment (not shown), the catheter may include a distal end and a balloon sized to be introduced into the thoracic duct. For example, the distal end may be advanced beyond a valve in the thoracic duct such that the balloon may be inflated beyond the valve. In addition or alternatively, the catheter may include one or more other features for securing and/or sealing distal to a valve, including one or more compliant rings, radial filaments/brushes, and/or other passive fixation devices (not shown) that may at least partially resist retraction or avoid spontaneous dislodgement of the catheter during use. In addition or alternatively, active fixation, such as suction, may be used to substantially fix the distal end of the catheter at a desired location, e.g., within the thoracic duct.

Figure 7A:
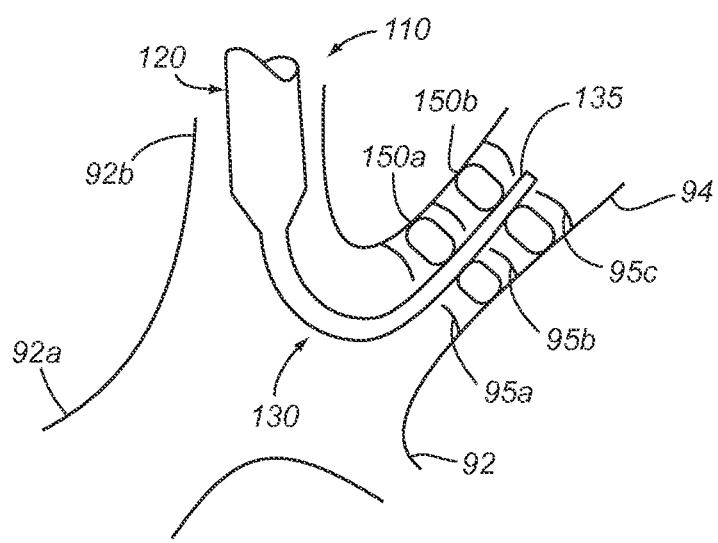
FIGS. 7A and 7B are details of a patient's body, showing a distal portion of another exemplary embodiment of an apparatus with a pair of balloons expanded within a thoracic duct of the patient on either side of a valve within the thoracic duct.
Figure 7B:
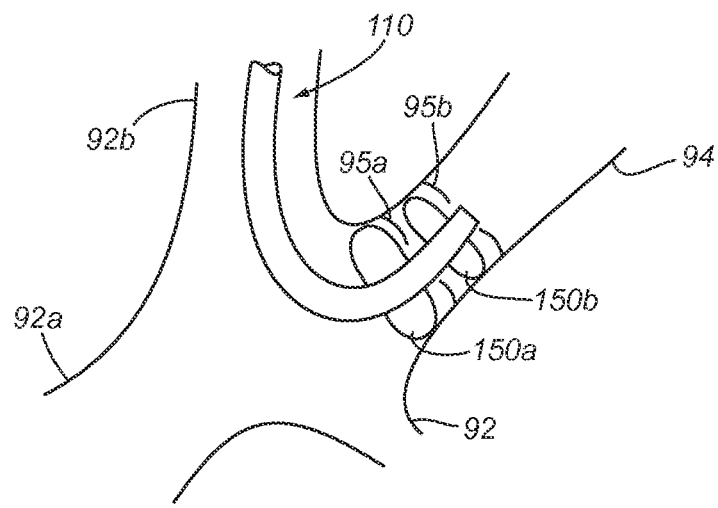

Turning to FIGS. 7A and 7B, another embodiment of a catheter 110 is shown that includes a pair of balloons 150 spaced apart axially from one another on a distal portion 130 of the catheter 130. The balloons 150 may communicate with a single inflation lumen (not shown) such that the balloons 150 may be inflated and/or collapsed substantially simultaneously. Alternatively, the balloons 150 may communicate with separate inflation lumens (also not shown) such that the balloons 150 may be inflated and/or collapsed independently of one another. The catheter 110 may have a size, length, and/or shape configured to be introduced and/or manipulated using a handle or hub on a proximal end (not shown) of the catheter 110, similar to other embodiments herein.

As shown in FIGS. 7A and 7B, a distal tip 135 of the catheter 110 may be introduced into the thoracic duct 94 until the balloons 150 pass beyond the terminal valve 95a. Optionally, as shown in FIG. 7A, the balloons 150 may be spaced apart sufficiently from one another such that the balloons may be provided on either side of the next valve 95b within the thoracic duct 94, i.e., with a proximal balloon 150a between a first and second valve 95a, 95b, and a distal balloon 150b between the second and third valves 95b, 95c. Such an arrangement of balloons 150 may provide enhanced stability for the distal portion 130 and/or improved sealing of the thoracic duct 94.

Optionally, the balloons 150 may be configured such that the balloons 150 may be positioned with a valve 95b located between the balloons 150. When the balloons 150 are inflated, they may squeeze or otherwise engage the valve 95b to enhance sealing of the thoracic duct 94 using the valve 95b in addition to the balloons 150 engaging the wall of the thoracic duct 94. In another option, shown in FIG. 7B, the balloons 150 may be positioned on either side of the terminal valve 95a such that the distal balloon 150b is positioned between the first and second valves 95a, 95b, and the proximal balloon 150a engages the ostium of the thoracic duct 94 outside the terminal valve 95a, which may reduce the risk of blood entering the thoracic duct 94 from the veins 92. Further alternatively, the balloons 150 may be slidably disposed relative to one another (not shown) such that they may be brought together or moved apart, e.g., to capture and/or release a valve positioned between them. Further alternatively, one or more balloons may include different surface properties, e.g. a lubricious distal surface (e.g., using a hydrophilic coating, lubrication, surface features, and the like), e.g., to facilitate valve crossing and a less lubricious proximal surface to, e.g. to decrease the chance of inadvertent removal.

Figure 8:
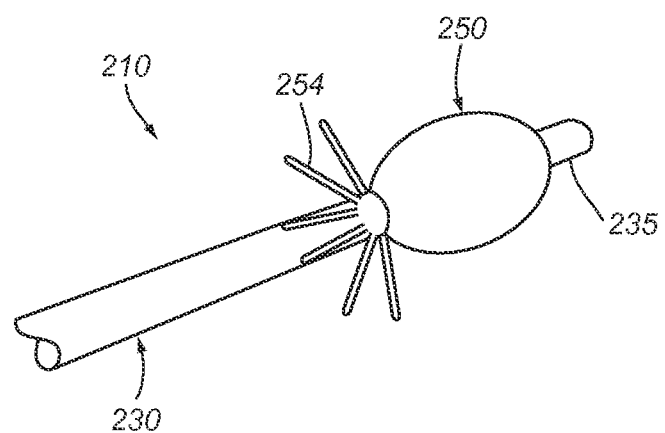
FIG. 8 is a detail showing a distal portion of another embodiment of a catheter including a plurality of expandable tines adjacent a balloon for anchoring the distal portion relative to a thoracic duct.

Turning to FIG. 8, still another embodiment of a catheter 210 is shown that includes a plurality of tines 254 on the distal portion 230 adjacent the balloon 250. The tines 254 may be biased to expand outwardly, but may be compressible inwardly, e.g., using an external sleeve or other constraint (not shown), which may be removed, e.g., after positioning the balloon 250 at a desired position within a thoracic duct (also not shown). When the tines 254 are deployed, they may engage the wall of the thoracic duct to anchor the distal portion 230 to prevent movement even if the balloon 250 is collapsed. The tines 254 may include substantially blunt free ends to engage the thoracic duct without penetrating or damaging the wall, or may include sharpened tips and/or barbs (not shown), which may be substantially permanently or indefinitely engage the wall of the thoracic duct. Thus, this embodiment may be used to secure the catheter 210 substantially indefinitely, e.g., for a long-term implant that is used to intermittently isolate the thoracic duct by expanding the balloon 250, e.g., to collect lymph.

When not needed, the balloon 250 may be collapsed allowing normal function of the thoracic duct while the tines 254 prevent migration of the catheter 210 from the thoracic duct. If desired, the catheter 210 may be removed, e.g., by directing a sheath or other tubular member (not shown) into the thoracic duct to recapture and/or otherwise collapse the tines 254.

Alternatively, other features may be provided on the catheter, e.g., in addition to or instead of the tines 254 to maintain the distal end of the catheter 210 (or any of the embodiments herein) in a desired position, e.g., within the thoracic duct. Exemplary features may include providing silicone or other anti-slip materials on the distal end, a Nitinol or other expandable anchoring structure, an anchor ring, and the like (not shown).

Figure 9A:
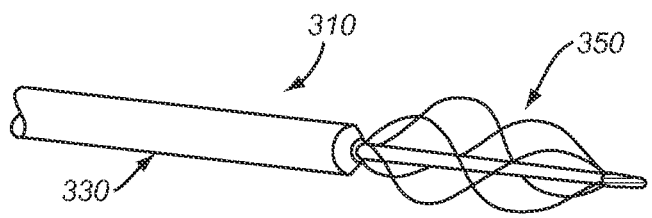
FIGS. 9A-9C are side and ends views of yet another embodiment of a catheter including a mechanically expandable member that is expandable from a collapsed configuration (FIG. 9A) to an enlarged configuration (FIGS. 9B and 9C) for isolating a thoracic duct.
Figure 9B:
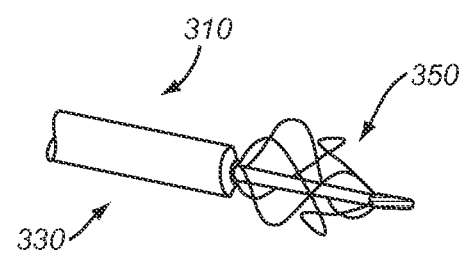
Figure 9C:
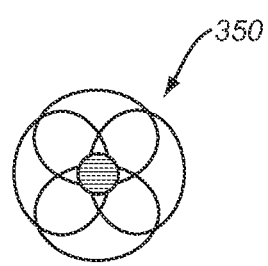

Turning to FIGS. 9A-9C, another embodiment of a catheter 310 is shown that includes an expandable frame 350 on a distal portion 330 including a set of wires or struts that may be manipulated from a proximal end (not shown) of the catheter 310. For example, an actuator on the proximal end (not shown) may be activated to direct the frame from a collapsed configuration (shown in FIG. 9A) to an enlarged configuration (shown in FIG. 9B). The size of the frame 350 may be sufficient to engage a wall of a thoracic duct when the distal portion 330 is introduced into the thoracic duct, as described elsewhere herein.

As shown in FIG. 9C, the frame 350 may carry a nonporous membrane that may be directed across the thoracic duct when the frame 350 is expanded to substantially seal the thoracic duct. Thus, the frame 350 may operate similar to the balloons described elsewhere herein, except that the frame 350 is mechanically actuated rather using fluid to inflate and collapse the balloons.

Figure 10:
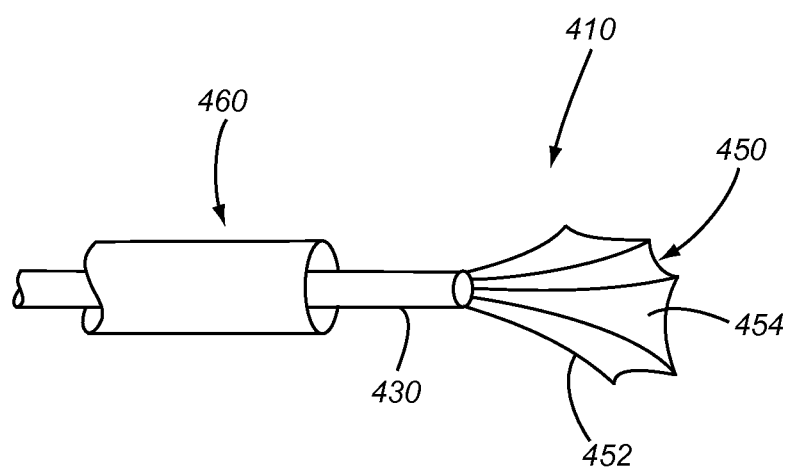
FIG. 10 is a side view of still another embodiment of a catheter including an expandable umbrella/hood shown in an expanded configuration upon deployment from a delivery sheath.

Turning to FIG. 10, yet another embodiment of a catheter 410 is shown that includes an expandable frame 450 on a distal portion 430 including a set of wires or struts 452 carrying a non-porous membrane 454. The frame 450 may be biased to an enlarged configuration, e.g., in which the struts are shaped to engage and/or enter the ostium of a thoracic duct, yet may be resiliently compressed into a delivery configuration, e.g., when placed within a delivery catheter 460. Alternatively, the frame 450 may be actuated from a proximal end (not shown) of the catheter 410, e.g., similar to the previous embodiments. The size of the frame 450 may be sufficient to engage the ostium adjacent the thoracic duct, or may be sized for introduction into the thoracic duct such that the membrane 454 sealingly engages the wall of the thoracic duct, e.g., when the distal portion 430 is introduced into the thoracic duct on either side of one or more valves, similar to other embodiments herein.

Turning to FIG. 5, the apparatus 8 shown in FIG. 1, or any of the other embodiments herein, may be part of a system 6 including one or more external components for performing a medical procedure, e.g., which may involve removing lymphatic fluid from the patient's body 90 via the thoracic duct 94, introducing agents or devices (not shown) into the thoracic duct 94, and/or infusing the removed lymphatic fluid, components thereof, and/or other agents into other locations within the patient's body 90. For example, one or more external devices may be provided that are coupled to the proximal end 22 of the catheter 10, e.g., for detecting, separating, collecting, and/or infusing lymphatic fluid and/or other fluids, as described in U.S. Publication No. 2011/0276023, the entire disclosure of which is expressly incorporated by reference herein. The external components may be provided integrated into a single device or may be provided as separate discrete components that are coupled to one another (e.g., along a fluid path, electrically, and/or otherwise).

In the example shown schematically in FIG. 5, the external components may include a detector or analyzer 60, a controller 62, a separator or filter 64, a waste container 66, a storage container 68, and an infusion device 70. One or more of the components may include a pump or source of vacuum or pressure, e.g., for removing fluid from the patient's body and/or delivering fluid into the patient's body 90 via the catheter 10, or infusing fluids via the infusion device 70, as described further below. In alternative embodiments, one or more of the components may be omitted. For example, the catheter 10 may simply be coupled directly to the storage container 68, e.g., with or without a source of vacuum to facilitate collection of lymphatic fluid (and any agents that end up within the lymphatic system).

The detector 60 may be coupled to the proximal end 22 of the catheter 10, e.g., to the port 23a on the handle 23, for receiving fluids that are drawn through the lumen 26 of the catheter 10 from the inlet port 36 in the distal tip 35 (not shown in FIG. 5, see, e.g., FIGS. 2A, 2B). The detector 60 may include one or more sensors (not shown), e.g., for distinguishing between lymphatic fluid and blood. In addition or alternatively, one or more sensors may be provided on the distal end 34 of the catheter 10, e.g., to detect when the thoracic duct is accessed and/or sealed from the venous system. In exemplary embodiments, the sensor(s) may include one or more optical sensors (e.g., for detecting the presence of red blood cells by light transmission or reflection characteristics), chemical sensors (e.g., for detecting one or more of pH, oxygen concentration, lactate, leukocyte esterase, and the like), sensors for measuring hematocrit, electrical sensors (e.g., for measuring impedance), temperature sensors, mechanical sensors (e.g., for detecting pressure waves, which may differ between the venous system and the thoracic duct; for flow detection, e.g., by Doppler ultrasound), filter devices sized to constituents of whole blood, and the like. In addition or alternatively, a sensor may be provided that is adapted to detect the presence of an exogenous marker introduced into the lymphatic system, such as a dye (e.g., methylene blue), an ingested marker, a fluorescent marker, and the like.

For example, a pump or other source of vacuum or pressure (not shown) within or coupled to the detector 60 may be selectively activated, e.g., by the controller 62 (or alternatively manually by a user, if desired), to remove fluid from the patient's body via the catheter 10 through the detector 60 to the separator 64. The controller 62 may automatically analyze sensor data from the sensors to identify whether the fluid is lymphatic fluid, blood, or other fluid.

For example, if the controller 62 determines that the fluid includes blood, the controller 62 may direct the fluid to the waste container 66, e.g., through the separator 64 or directly. In addition or alternatively, if the controller 62 detects the presence of a significant amount blood in the fluid (based on data from the detector 60 or otherwise) or detects a loss of seal (e.g., due a sudden pressure change in the fluid being removed via the catheter 10), the controller 62 may shut down the pump, close a shut-off valve (not shown) in the detector 60, or otherwise stop flow of fluid from the catheter 10 into the detector 60 and/or the rest of the system 6. This safety mechanism may be active, i.e., shut down automatically, or passive, i.e., merely warn the user.

In an exemplary embodiment, the separator 64 may include a valve (not shown) including an inlet 64a that communicates with the detector 60, a first outlet 64b communicating with the storage container 68, and a second outlet 64c communicating with the waste container 66. The valve may be selectively operable between the first and second outlets 64b, 64c by the controller 62, e.g., to direct undesired fluid, e.g., blood, to the waste container 66, and desired fluid, e.g., lymphatic fluid or components thereof, to the storage container 68. Alternatively, or in addition, the separator 64 may include one or more devices for separating and/or filtering various components of lymphatic fluid, including various types of cells, proteins, electrolytes, water, and/or other constituent parts of lymphatic fluid, and/or target agents that have transited into the lymphatic system. For example, chemotherapy or other agents may be substantially separated from other components in order to selectively remove the agents from a patient's body, e.g., to avoid systemic delivery of the agents, as described elsewhere herein.

If the controller 62 confirms that the fluid is lymphatic fluid, the controller 62 may activate the separator 64 to direct the lymphatic fluid or components of the lymphatic fluid into the storage container 68. For example, if the entire lymphatic fluid is to be collected, the separator 64 may simply divert the fluid into the storage container 68. Alternatively, it may be desirable to separate certain constituents of the removed fluid, e.g., lymphatic fluid, particular cells, proteins, and the like, and/or agents previously introduced into the patient's body. For example, the separator 64 may include one or more of a mechanical filtration system, an osmotic gradient system, a concentration gradient system, a centrifuge, and the like to separate the desired components from the rest of the fluid. Once separated, the desired components may be delivered to the storage container 68, while the rest of the fluid is delivered to the waste container 66.

Optionally, the controller 62 or other components of the system 6 may monitor the flow to keep track of the amount of fluid extracted and/or to stop after a predetermined amount of fluid is extracted. In addition or alternatively, the controller 62 may operate the pump, vacuum source, valve, and/or other components of the system 6 periodically or otherwise intermittently, e.g., to allow reaccumulation of fluid within the lymphatic vessels.

For example, as shown in FIG. 5, an infusion catheter 70 may be provided that includes a proximal end 70a coupled to the storage container 68, and a distal end 70b sized for delivering the stored fluid into the patient's body 90. Alternatively, the lymphatic fluid removed from the patient's body may be reinfused, e.g., after separation, treatment, and the like, back into the thoracic duct 94 using the catheter 10 already positioned in the thoracic duct 94. In addition or alternatively, the catheter 10 may be used to infuse other fluid directly into the thoracic duct 94, e.g., as described further elsewhere herein.

For example, the catheter 10 may include a single infusion lumen, e.g., for removing lymphatic fluid and returning any desired fluids back into the patient's body. Alternatively, the catheter 10 may include multiple lumens (not shown), e.g., an aspiration lumen for removing lymphatic fluid and an infusion lumen for delivering fluids (e.g., to the thoracic duct and/or adjacent vein), such as treated lymphatic fluid and/or other diagnostic or therapeutic compounds. Such lumens may terminate at the distal portion of the catheter 30 and/or more proximally. For example, the aspiration lumen may include an inlet distally beyond the balloon, e.g., for aspirating fluid from the isolated thoracic duct, while the infusion lumen may include an outlet proximal to the balloon, e.g., to provide a fluid channel into the venous system adjacent to the thoracic duct. In addition or alternatively, the catheter 10 may include a working lumen sized for receiving auxiliary devices therethrough (not shown), e.g., larger than the infusion lumen(s) for receiving one or more guidewires, auxiliary catheters, and the like (not shown). If the catheter 10 includes one or more balloons, e.g., balloon 50 shown in FIG. 1, the catheter 10 may also include one or more inflation lumens (not shown), e.g., adjacent the aspiration, infusion, and/or working lumen(s), for inflating and/or collapsing the balloon(s) together or independently of one another, as described elsewhere herein.

The catheters, systems, and methods described herein may be used to perform a variety of procedures within the patient's body, e.g., involving accessing the thoracic duct, removing lymphatic fluid from the thoracic duct, and/or infusing or reinfusing fluids into the thoracic duct. For example, agents delivered to other locations within a patient's body may transit into the thoracic duct, and the fluid may be removed to prevent such agents from entering the patient's venous system, which may otherwise risk systemic exposure of the agents to the patient.

Figures 11, 11A:
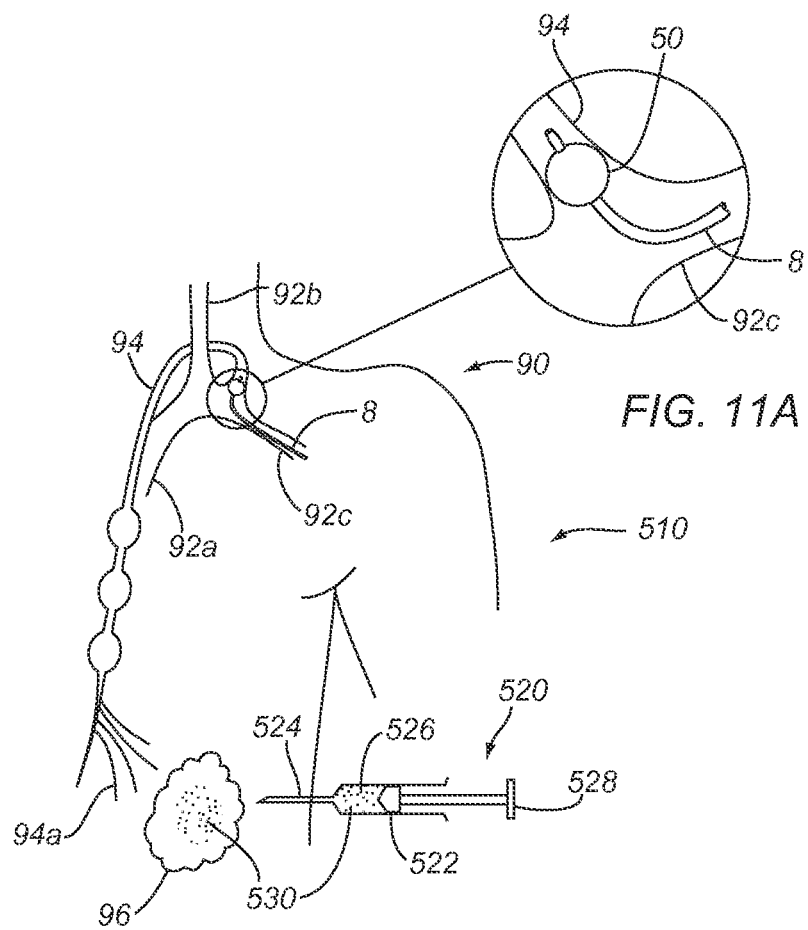
FIG. 11 is a cross-section of a patient's body showing a schematic of an exemplary system for delivering therapeutic and/or diagnostic agents into the patient's body.
FIG. 11A is a detail of the patient's body of FIG. 11 showing a device isolating the patient's thoracic duct from the patient's venous system.

Turning to FIGS. 11 and 11A, an exemplary embodiment of a system 510 is shown that includes a syringe 520 including a chemotherapy drug and/or other therapeutic and/or diagnostic agent 530, and an apparatus 8 for sealing the thoracic duct and/or removing fluid from the thoracic duct (which may be any of the embodiments described elsewhere herein or in the applications incorporated by reference), e.g., to prevent systemic exposure of the agent(s) 530 delivered using the syringe 520. The system 510 may be used to temporarily access and/or isolate the thoracic duct 94. Alternatively, the apparatus 8 may be implanted entirely within the patient's body 90 (not shown), e.g., to allow chronic access to the thoracic duct 94, allow selective isolation and/or removal of lymphatic fluid.

Generally, the syringe 520 includes a barrel 522 defining an interior 524 containing the agent(s) 530, a needle 526 coupled to the barrel 522, and a plunger 528 slidable within the barrel 522 for delivering the agent(s) 530 within the barrel 522 through the needle 526 into a patient's body 90, as described further below. Alternatively, other delivery devices (not shown) may be used for localized delivery of the agent(s) within a target treatment site within the patient's body 90. For example, a catheter (not shown) may be provided that includes a distal end sized for introduction into the patient's body 90, e.g., into the patient's vasculature or other body lumens, which may include a lumen for delivering the agent(s) within a target body lumen e.g., within micro-bubbles, micro-particles, and the like (not shown), and/or may include a needle (also not shown) deployable from the catheter for delivering the agent(s) into tissue adjacent a body lumen within which the catheter distal end is positioned. In the exemplary embodiment shown in FIG. 5, the agent(s) 530 may be injected directly into or adjacent a tumor 96, e.g., within a patient's breast, ovary, lung, gastrointestinal (GI) tract, and the like. In other alternatives, the agent(s) may be injected into an artery supplying blood to a tumor and/or the agent(s) may be taken orally.

The agent(s) 530 may include particles sized and/or otherwise formulated for preferential uptake into the lymphatic system. For example, with reference to FIG. 5, at the level of the capillary bed, lymphatic channels 94a consist of overlapping fenestrations, permitting uptake of macrolecules and compounds too large to return through venous capillaries. If the particles of the agent(s) 530 have an outer diameter or other cross-section larger than about thirty to forty nanometers (30-40 nm) and smaller than about one hundred nanometers (100 nm), the particles may pass freely from the interstitium into lymphatic capillary channels 94a and transit into the thoracic duct 94. In contrast, compounds larger than about one hundred nanometers (100 nm) remain confined to the site of injection while compounds smaller than about forty nanometers (40 nm) may pass into venous capillaries.

For example, liposomal formulations of existing chemotherapy agents may be used in which the agents are encapsulated within lipid membranes, e.g., within a micelle, to provide particles having appropriate sizes. Alternatively, large lipophilic moieties or functional groups may be attached, at least temporarily, to the agent(s). In an exemplary embodiment, a chemotherapy agent may be encapsulated in a lipid membrane having an outer diameter between about twenty and one hundred nanometers (20-100 nm) or between about forty and fifty nanometers (40-50 nm) such that the agent may preferentially pass into the lymphatic capillary channels 94 (rather than the venous capillaries, not shown) and transit into the thoracic duct 94. In addition or alternatively, the agents may be modified or augmented using one or more additional methods, such as pegylation, positive or negative charging, or dye or fluorescent reporter conjugation.

The systems and methods herein may be particularly useful when treating cancers or metastases in locations significantly drained by the lymphatic system and/or in close proximity to the thoracic duct, e.g., the breast, lung, GI tract, and the like. In addition or alternatively, the systems and methods herein may be used to treat cancers that preferentially reside within the lymphatic system, including lymph nodes, such as lymphoma, and other blood borne malignancies, lymphatic and lymph node metastases derived from other primary tumors, and the like.

In an exemplary method, shown in FIG. 11, the syringe 520 may be used to inject the agent(s) 530 directly into or adjacent a tumor 96, e.g., via percutaneous access, i.e., by sticking the needle 522 through the patient's skin and intervening tissue into the tumor 96. Once the needle 522 is positioned within (or adjacent) the tumor 96, the plunger 528 may be depressed to inject the agent(s) 530 into the target site, and then the needle 522 may be removed, as shown. Alternatively, the agent(s) 530 may be introduced intravenously, intra-arterially, or into other body cavities. In a further alternative, the agent(s) 530 may be introduced directly into the lymphatic system in either antegrade or retrograde fashion.

Before or after delivering the agent(s) 530, an apparatus 8 may be used to temporarily isolate the thoracic duct 94 from the patient's venous system, e.g., at the junction of the left internal jugular vein 92b and left subclavian vein 92c, as best seen in FIG. 11A. For example, the apparatus 8 may be introduced into the patient's venous system from a percutaneous entry site (not shown) and advanced into the junction of the left internal jugular vein 92b and left subclavian vein 92c. As shown in FIG. 11A, a balloon 50 of the apparatus 8 may be positioned within the ostium of the thoracic duct 94 (e.g., beyond one or more valves of the thoracic duct 94, not shown) and then expanded to substantially seal the thoracic duct 94. Alternatively, other devices and methods may be used to isolate and/or access the thoracic duct 94, e.g., similar to the embodiments described elsewhere herein and in the applications incorporated by reference.

In an exemplary embodiment, the apparatus 8 may be introduced into the patient's body 90 immediately after injecting the agent(s) 530 and used to isolate the thoracic duct 94 for a predetermined time, e.g., until the agent(s) 530 are fully metabolized or otherwise cleared by the patient's body. As the agent(s) 530 preferentially pass from the tumor 96 into the lymphatic capillary channels and transit into the thoracic duct 94, the apparatus 8 may prevent the agent(s) from entering the patient's venous system.

Optionally, flow into and/or through the thoracic duct 94 may be monitored and/or regulated using the system 510, e.g., using a system similar to the system 6 shown in FIG. 5 and described elsewhere herein. For example, subsequent to delivery of the agent(s) 530, output from the thoracic duct 94 may be monitored using the system 510, e.g., to detect when the particles of the agent(s) 530 have entered the thoracic duct 94 using the apparatus 8 positioned within the thoracic duct 94. Before the agent(s) 530 are detected, the system 510 may regulate flow through the thoracic duct 94, e.g., automatically or manually deflating the balloon 50 to allow lymphatic fluid (without any agent(s) 530) to return to the patient's venous system.

Alternatively, the system 510 may be used to divert all of the lymphatic fluid from the thoracic duct 94, e.g., via a lumen of the apparatus 8 to one or more external components, which may monitor and/or regulate flow of lymphatic fluid back into the patient's body 90, e.g., via a lumen of the apparatus 8 or via intravenously using a needle, similar to the infusion device 70 shown in FIG. 5. For example, if the system 510 determines the lymphatic fluid is agent-free, all of the fluid may be returned to the patient's body 90, e.g., using the apparatus 8 or intravenously. Once the presence of an agent is detected, the system 510 may discard all of the fluid, may filter the fluid to remove the agent(s), may deactivate the agent(s), and return the remaining fluid to the patient's body 90, e.g., similar to the system 6.

Optionally, the system 510 may include a source of vacuum, pump, or other device (not shown) to facilitate removing lymphatic fluid from the thoracic duct 94, e.g., using the apparatus 8. For example, after a predetermined time of exposure, flow through the thoracic duct 94 may be increased to accelerate removal of the agent(s) from the target site into the lymphatic system.

With continued reference to FIG. 11, in this manner the system 510 may enable controlling exposure time and/or transit of toxic chemotherapeutic agents 5330 delivered into a tumor 96, e.g., within a breast or other tissue structure (not shown). For example, the effects of agent(s) 530 may be concentrated in the local tissue e.g., at the site of the tumor 96 where the agent(s) may be delivered, by slowing transit of the agent(s) 530 into the lymphatic system. As an example, an agent, designed for preferential uptake to the lymphatic system, may be introduced locally in or around the site of a breast tumor and the rate of local depletion may be modulated by controlling the flow rate through the thoracic duct 94, e.g. by selective occlusion or flow restriction using the apparatus 8 and system 510. Optionally, concentration of the agent(s) 530 present in the removed fluid may be monitored to control exposure time and/or otherwise assessing and controlling therapy. Thus, the system 510 may be used to control the time that the agent(s) remain at the target site may be controlled indirectly by controlling flow into the thoracic duct 94 and/or through the lymphatic system.

Once the agent(s) 530 enter the thoracic duct 94, the system 510 may be used to prevent the agent(s) from entering the venous system, thereby minimizing exposure to the remainder of the patient's body 90 and thus limiting toxicity. Such systems and methods may be particularly useful for treating cancers or metastases in locations significantly drained by the lymphatic system and/or in close proximity to the thoracic duct 94, e.g., cancers of the breast, lung, GI tract, and the like.

In another embodiment, the system 510 may be used to treat cancers that reside within the lymphatic system itself, including within the lymph nodes, such as lymphoma, and/or to treat other blood borne malignancies, lymphatic and lymph node metastases derived from other primary tumors, and the like. For example, the apparatus 8 may be used to isolate the thoracic duct 94 and deliver one or more agent(s) into the thoracic duct 94 in a retrograde manner to treat cancers within the lymphatic system.

In another embodiment, the system 510 may be used to modulate the lymphatic system before delivering one or more agents into the patient's body. For example, before injecting agent(s) 530 into a tumor 96, the apparatus 8 may be introduced into the patient's body 90 and used to isolate the thoracic duct 94 and remove lymphatic fluid, e.g. to decrease volume and/or pressure within the lymphatic system and at least transiently increase uptake of agent from tissue into the lymphatic system. Alternatively, or in addition, lymphatic fluid, e.g., without contamination by the agent(s), may be removed before agent delivery and reinfused after completion of treatment.

Further alternatively, the lymphatic system in proximity to an organ targeted for agent delivery may be substantially isolated in order to protect other organs. For example, distal end of the apparatus 8 (or other catheter or device) may be sized (e.g., having a desired length and sufficiently small diameter) to pass deep into the thoracic duct 94. The distal end of the apparatus may be passed retrograde into the ostium of the thoracic duct 94 toward the target organ (e.g., a breast, lungs, and the like), and the balloon 50 may be expanded within the thoracic duct 94 at a location adjacent the target organ to further isolate collected agent.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A method for treating a patient having a body including vasculature and a lymphatic system including a thoracic duct, comprising:
    injecting one or more therapeutic agents directly into a target treatment site outside the lymphatic system within the patient's body, the one or more therapeutic agents comprising particles sized for preferential transit into the lymphatic system;
    introducing a distal end of a tubular member into the vasculature via a percutaneous access site;
    advancing the tubular member until the distal end of the tubular member is disposed within a junction of a left internal jugular vein and left subclavian vein and adjacent the thoracic duct;
    sealing the thoracic duct using the distal end of the tubular member to isolate the thoracic duct from the junction; and
    removing fluid from the thoracic duct through the tubular member to a location exterior to the patient's body, thereby removing particles from the one or more therapeutic agents that have transited into the thoracic duct.

2. The method of claim 1, wherein the particles have an outer cross-section larger than thirty nanometers (30 nm).

3. The method of claim 2, wherein the particles have an outer cross-section smaller than one hundred nanometers (100 nm).

4. The method of claim 1, wherein the one or more therapeutic agents comprise a chemotherapy agent encapsulated within a lipid membrane.

5. The method of claim 1, further comprising:
    removing the particles from the removed fluid via one or more external components exterior to the patient's body; and returning at least a portion of the removed fluid from the one or more external components into the thoracic duct through the tubular member after removing the particles.

6. The method of claim 1, wherein sealing the thoracic duct comprises:
   manipulating the tubular member to direct the distal end into the thoracic duct; and
   expanding an expandable member on the distal end to isolate the thoracic duct from the patient's vasculature.

7. The method of claim 1, further comprising analyzing the removed fluid to detect whether the one or more therapeutic agents are present in the removed fluid, thereby identifying when the one or more therapeutic agents have transited into the thoracic duct.

8. The method of claim 7, wherein the removed fluid is analyzed to determine a concentration of the one or more therapeutic agents in the removed fluid.

9. The method of claim 8, further comprising returning the removed fluid into the patient's body before the one or more therapeutic agents have been detected in the removed fluid.

10. The method of claim 1, further comprising controlling a flow rate of fluid removed from the thoracic duct to control a resident time of the one or more therapeutic agents at the target treatment site.

11. The method of claim 1, wherein the target treatment site comprises a tumor.

12. The method of claim 1, wherein injecting the one or more therapeutic agents comprises injecting one or more chemotherapy agents into the target treatment site to treat cancer at the target treatment site.

13. A method for treating a patient having a body including a lymphatic system including a thoracic duct, comprising:
   injecting a therapeutic agent into interstitial tissue adjacent a target site within a patient's body outside the thoracic duct, the therapeutic agent sized for preferential transit into the lymphatic system; and
   subsequently modulating flow from the thoracic duct to modulate one or both of resident time and concentration of the therapeutic agent within the tissue at the target site.

14. The method of claim 13, wherein the therapeutic agent moves into, remains within, or transits within the lymphatic system from the target site.

15. The method of claim 13, wherein modulating flow from the patient's thoracic duct comprises collecting lymph from the thoracic duct, the method further comprising:
   monitoring agent concentration within the collected lymph; and
   discontinuing collecting lymph when the agent concentration reaches a predetermined threshold.

16. The method of claim 15, wherein collecting lymph comprises:
   introducing a tubular member into vasculature within the patient's body;
   using the tubular member to isolate the thoracic duct from the vasculature; and
   collecting the lymph from the thoracic duct using the tubular member.

17. A method for treating a patient having a body including a lymphatic system including a thoracic duct, comprising:
   injecting one or more therapeutic agents into interstitial tissue within the patient's body outside the thoracic duct, the one or more therapeutic agents sized for preferential transit into the lymphatic system; and
   modulating lymph output from the thoracic duct to manipulate delivery of the one or more therapeutic agents within the patient's body.

18. The method of claim 17, wherein modulating lymph output comprises at least one of modulating flow and volume of lymph from the thoracic duct.

19. The method of claim 17, wherein modulating lymph output comprises modifying or eliminating a natural return path of lymph into a venous system of the patient's body.

20. The method of claim 17, wherein modulating lymph output comprises:
   introducing a tubular member into vasculature within the patient's body;
   using the tubular member to isolate the thoracic duct from the vasculature; and
   selectively removing lymph from the thoracic duct using the tubular member.

21. The method of claim 17, wherein the interstitial tissue is located in or around a tumor.

22. The method of claim 21, wherein the tumor is located in one of the patient's breast, ovary, lung, and gastrointestinal (GI) tract.

* * * * *